(12) United States Patent
Shinkawa et al.

(10) Patent No.: US 12,426,828 B2
(45) Date of Patent: Sep. 30, 2025

(54) DETECTION OF COGNITIVE IMPAIRMENT USING SPEECH FEATURE DISTRIBUTION

(71) Applicant: INTERNATIONAL BUSINESS MACHINES CORPORATION, Armonk, NY (US)

(72) Inventors: Kaoru Shinkawa, Hachioji (JP); Yasunori Yamada, Kawaguchi (JP); Masatomo Kobayashi, Tokyo (JP)

(73) Assignee: International Business Machines Corporation, Armonk, NY (US)

( * ) Notice: Subject to any disclaimer, the term of this patent is extended or adjusted under 35 U.S.C. 154(b) by 706 days.

(21) Appl. No.: 17/644,147

(22) Filed: Dec. 14, 2021

(65) Prior Publication Data

US 2023/0181093 A1 Jun. 15, 2023

(51) Int. Cl.
| | |
|---|---|
| G10L 25/66 | (2013.01) |
| A61B 5/00 | (2006.01) |
| A61B 5/16 | (2006.01) |
| G10L 15/02 | (2006.01) |
| G10L 15/04 | (2013.01) |
| G10L 15/06 | (2013.01) |
| G10L 15/22 | (2006.01) |
| G16H 50/20 | (2018.01) |

(52) U.S. Cl.
CPC .......... *A61B 5/4088* (2013.01); *A61B 5/4803* (2013.01); *A61B 5/742* (2013.01); *A61B 5/7475* (2013.01); *G10L 15/02* (2013.01); *G10L 15/04* (2013.01); *G10L 15/063* (2013.01); *G10L 15/22* (2013.01); *G10L 25/66* (2013.01); *G16H 50/20* (2018.01)

(58) Field of Classification Search
CPC ............ G10L 25/66; G10L 15/02; A61B 5/16
See application file for complete search history.

(56) References Cited

U.S. PATENT DOCUMENTS

| | | |
|---|---|---|
| 2019/0304484 A1 | 10/2019 | Shinkawa |
| 2020/0229752 A1* | 7/2020 | Sumi .................... A61B 5/4803 |

(Continued)

FOREIGN PATENT DOCUMENTS

| | | |
|---|---|---|
| JP | 6804779 B2 | 12/2020 |
| WO | 2012045774 A1 | 4/2012 |
| WO | 2020128542 A1 | 6/2020 |

OTHER PUBLICATIONS

Rohanian, Morteza, Julian Hough, and Matthew Purver. "Alzheimer's dementia recognition using acoustic, lexical, disfluency and speech pause features robust to noisy inputs." arXiv preprint arXiv:2106.15684 (Jun. 2021). (Year: 2021).*

(Continued)

*Primary Examiner* — Jialong He
(74) *Attorney, Agent, or Firm* — Elliot J. Shine (57) ABSTRACT

A method, computer system, and a computer program product for speech feature distribution is provided. The present invention may include receiving two or more speech samples from a user. The present invention may include dividing the two or more speech samples into a a plurality of pause segments. The present invention may include determining a pause duration for each of the plurality of pause segments. The present invention may include determining a distribution of pause durations. The present invention may include determining a distance between the distribution of pause durations.

20 Claims, 5 Drawing Sheets

(56) References Cited

U.S. PATENT DOCUMENTS

| | | | |
|---|---|---|---|
| 2020/0327882 A1 | 10/2020 | Vairavan | |
| 2022/0039741 A1* | 2/2022 | Gosztolya | A61B 5/4803 |
| 2022/0369976 A1* | 11/2022 | Abbas | A61B 5/7264 |
| 2023/0233136 A1* | 7/2023 | Lee | A61B 5/4064 600/301 |

OTHER PUBLICATIONS

Yamada, Yasunori, et al. "Tablet-based automatic assessment for early detection of Alzheimer's disease using speech responses to daily life questions." Frontiers in Digital Health 3 (Mar. 2021): 653904. (Year: 2021).*

Kobayashi, Masatomo, et al. "Effects of age-related cognitive decline on elderly user interactions with voice-based dialogue systems." Human-Computer Interaction—INTERACT 2019: 17th IFIP TC 13 International Conference, Paphos, Cyprus, Sep. 2-6, 2019. (Year: 2019).*

Yamada, "Daily chats with AI could help spot early signs of Alzheimer's", [online] https://research.ibm.com/blog/ai-chats-spot-alzheimers; published in 2021. (Year: 2021).*

Yamada, Yasunori, et al. "A mobile application using automatic speech analysis for classifying Alzheimer's disease and mild cognitive impairment." Computer Speech & Language 81 (2023): 101514. (Year: 2023).*

Hall, "Using tablet-based assessment to characterize speech for individuals with dementia and mild cognitive impairment: preliminary results" (Year: 2019).*

Hall, et al., "Using Tablet-Based Assessment to Characterize Speech for Individuals with Dementia and Mild Cognitive Impairment: Preliminary Results," AMIA Jt Summits Transl Sci Proceedings, 2019, pp. 34-43, Retrieved from the Internet: <URL: https://www.ncbi.nlm.nih.gov/pmc/articles/PMC6568131/>.

König, et al., "Automatic speech analysis for the assessment of patients with predementia and Alzheimer's disease," Alzheimer's & Dementia: Diagnosis, Assessment & Disease Monitoring, Mar. 2015, pp. 112-124, doi: 10.1016/j.dadm.2014.11.012, Retrieved from the Internet: <URL: https://www.ncbi.nlm.nih.gov/pmc/articles/PMC4876915/>.

Mell, et al., "The NIST Definition of Cloud Computing", National Institute of Standards and Technology, Special Publication 800-145, Sep. 2011, 7 pages.

Roark, et al., "Spoken Language Derived Measures for Detecting Mild Cognitive Impairment," IEEE Transactions on Audio, Speech, and Language Processing, Feb. 7, 2011, pp. 2081-2090, vol. 19, Issue 7, DOI: 10.1109/TASL.2011.2112351, Retrieved from the Internet: <URL: https://ieeexplore.ieee.org/document/5710404>.

Toth, et al., Automatic Detection of Mild Cognitive Impairment from Spontaneous Speech using ASR, Interspeech [conference paper], Sep. 2015, 6 pages, DOI:10.21437/Interspeech.2015-568, Retrieved from the Internet: <URL: https://www.researchgate.net/publication/281089548_Automatic_Detection_of_Mild_Cognitive_Impairment_from_Spontaneous_Speech_using_ASR>.

* cited by examiner

DETECTION OF COGNITIVE IMPAIRMENT USING SPEECH FEATURE DISTRIBUTION

BACKGROUND

The present invention relates generally to the field of computing, and more particularly to speech feature distribution.

Changes in speech patterns may be one observation of patients suffering from cognitive impairments. Various speech analysis techniques may be utilized to detect changes in speech patterns, as a screening tool in identifying early stages of cognitive impairments, such as, but not limited to, MCI (mild cognitive impairment) and/or prodromal AD (Alzheimer's disease), amongst other cognitive impairments. One of the various speech analysis techniques which may be utilized is pause duration.

Pause duration may be utilized as an indicator of cognitive deficits, whereby a longer pause by a patient may indicate a higher likelihood the patient may suffer from a cognitive impairment.

SUMMARY

Embodiments of the present invention disclose a method, computer system, and a computer program product for speech feature distribution. The present invention may include receiving two or more speech samples from a user. The present invention may include dividing the two or more speech samples into a plurality of pause segments. The present invention may include determining a pause duration for each of the plurality of pause segments. The present invention may include determining a distribution of pause durations. The present invention may include determining a distance between the distribution of pause durations.

BRIEF DESCRIPTION OF THE SEVERAL VIEWS OF THE DRAWINGS

These and other objects, features and advantages of the present invention will become apparent from the following detailed description of illustrative embodiments thereof, which is to be read in connection with the accompanying drawings. The various features of the drawings are not to scale as the illustrations are for clarity in facilitating one skilled in the art in understanding the invention in conjunction with the detailed description. In the drawings.

DETAILED DESCRIPTION

Detailed embodiments of the claimed structures and methods are disclosed herein; however, it can be understood that the disclosed embodiments are merely illustrative of the claimed structures and methods that may be embodied in various forms. This invention may, however, be embodied in many different forms and should not be construed as limited to the exemplary embodiments set forth herein. Rather, these exemplary embodiments are provided so that this disclosure will be thorough and complete and will fully convey the scope of this invention to those skilled in the art. In the description, details of well-known features and techniques may be omitted to avoid unnecessarily obscuring the presented embodiments.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The following described exemplary embodiments provide a system, method and program product for speech feature distribution. As such, the present embodiment has the capacity to improve the technical field of detecting cognitive impairments by generating quantitative indicators of cognitive impairments based on distances between distributions of speech features extracted from two or more tasks. More specifically, the present invention may include receiving two or more speech samples from a user. The present invention may include dividing the two or more speech samples into a plurality of utterance segments and a plurality of pause segments. The present invention may include determining a pause duration for each of the plurality of pause segments. The present invention may include determining a distribution of pause durations. The present invention may include determining a distance between the distribution of pause durations.

As described previously, changes in speech patterns may be one observation of patients suffering from cognitive impairments. Various speech analysis techniques may be utilized to detect changes in speech patterns, as a screening tool in identifying early stages of cognitive impairments, such as, but not limited to, MCI (mild cognitive impairment) and/or prodromal AD (Alzheimer's disease), amongst other cognitive impairments. One of the various speech analysis techniques which may be utilized is pause duration.

Pause duration may be utilized as an indicator of cognitive deficits, whereby a longer pause by a patient may indicate a higher likelihood the patient may suffer from a cognitive impairment.

Therefore, it may be advantageous to, among other things, receive two or more speech samples from a user, divide the two or more speech samples into a plurality of utterance segments and a plurality of pause segments, determine a pause duration for each of the plurality of pause segments, determine a distribution of pause durations, and determine a distance between the distribution of pause durations. These steps may be advantageous in determining the probability in which the user may be suffering from a cognitive impairment based on the sensitivity to different tasks which may be identified utilizing the distance between the distribution of pause durations.

According to at least one embodiment, the present invention may improve the identification of early stages of cognitive impairment based on distances between distributions of speech features.

According to at least one embodiment, the present invention may improve obtaining quantitative indicators of possible cognitive deficits which may be resistant to inter-individual variability using distances between distributions of a specific speech feature extracted from two or more tasks. The distances between distributions of the specific speech feature may be utilized in identifying cognitive impairments if the user is more sensitive to different tasks.

According to at least one embodiment, the present invention may improve utilizing sensitivity to differences in cognitive tasks as opposed to comparing speech features from users which may be more susceptible to inter-individual variability, depending on pause duration as opposed to subtle changes in cognitive functioning.

According to at least one embodiment, the present invention may improve the identification of mild cognitive impairments in a user by comparing the distance of pause duration statistics between two tasks as opposed to using the mean pause duration in a single task. The present invention may also utilize additional speech features from two or more tasks rather than utilizing single-task features. Traditional single-task features may be determined utilizing mean pause duration and/or pause duration standard deviation which may be comparatively inefficient to the two or more task method in terms of discriminating mean confidence interval and/or healthy control, for individuals with a diagnosed cognitive impairment versus individuals with no diagnosed cognitive impairment.

Figure 1:
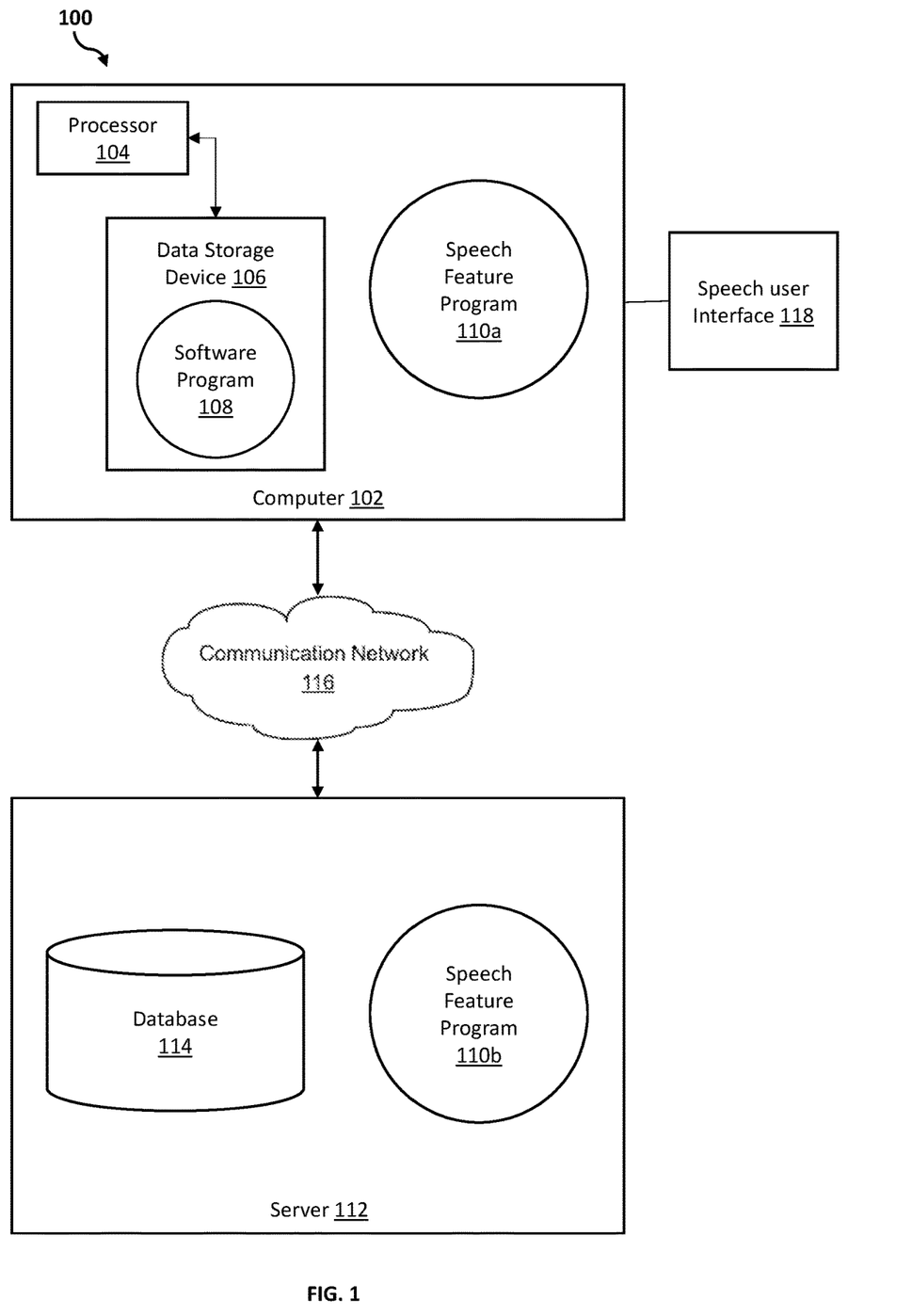
FIG. 1 illustrates a networked computer environment according to at least one embodiment.

Referring to FIG. 1, an exemplary networked computer environment 100 in accordance with one embodiment is depicted. The networked computer environment 100 may include a computer 102 with a processor 104 and a data storage device 106 that is enabled to run a software program 108 and a speech feature program 110a. The networked computer environment 100 may also include a server 112 that is enabled to run a speech feature program 110b that may interact with a database 114 and a communication network 116. The networked computer environment 100 may include a plurality of computers 102 and servers 112, only one of which is shown. The communication network 116 may include various types of communication networks, such as a wide area network (WAN), local area network (LAN), a telecommunication network, a wireless network, a public switched network and/or a satellite network. It should be appreciated that FIG. 1 provides only an illustration of one implementation and does not imply any limitations with regard to the environments in which different embodiments may be implemented. Many modifications to the depicted environments may be made based on design and implementation requirements.

The client computer 102 may communicate with the server computer 112 via the communications network 116. The communications network 116 may include connections, such as wire, wireless communication links, or fiber optic cables. As will be discussed with reference to FIG. 3, server computer 112 may include internal components 902a and external components 904a, respectively, and client computer 102 may include internal components 902b and external components 904b, respectively. Server computer 112 may also operate in a cloud computing service model, such as Software as a Service (SaaS), Platform as a Service (PaaS), or Infrastructure as a Service (IaaS). Server 112 may also be located in a cloud computing deployment model, such as a private cloud, community cloud, public cloud, or hybrid cloud. Client computer 102 may be, for example, a mobile device, a telephone, a personal digital assistant, a netbook, a laptop computer, a tablet computer, a desktop computer, or any type of computing devices capable of running a program, accessing a network, and accessing a database 114. According to various implementations of the present embodiment, the speech feature program 110a, 110b may interact with a database 114 that may be embedded in various storage devices, such as, but not limited to a computer/mobile device 102, a networked server 112, or a cloud storage service.

According to the present embodiment, a user using a client computer 102 or a server computer 112 may use the speech feature program 110a, 110b (respectively) to generate quantitative indicators of cognitive impairment based on distances between distributions of speech features extracted from two or more tasks. The speech feature method is explained in more detail below with respect to FIG. 2.

Figure 2:
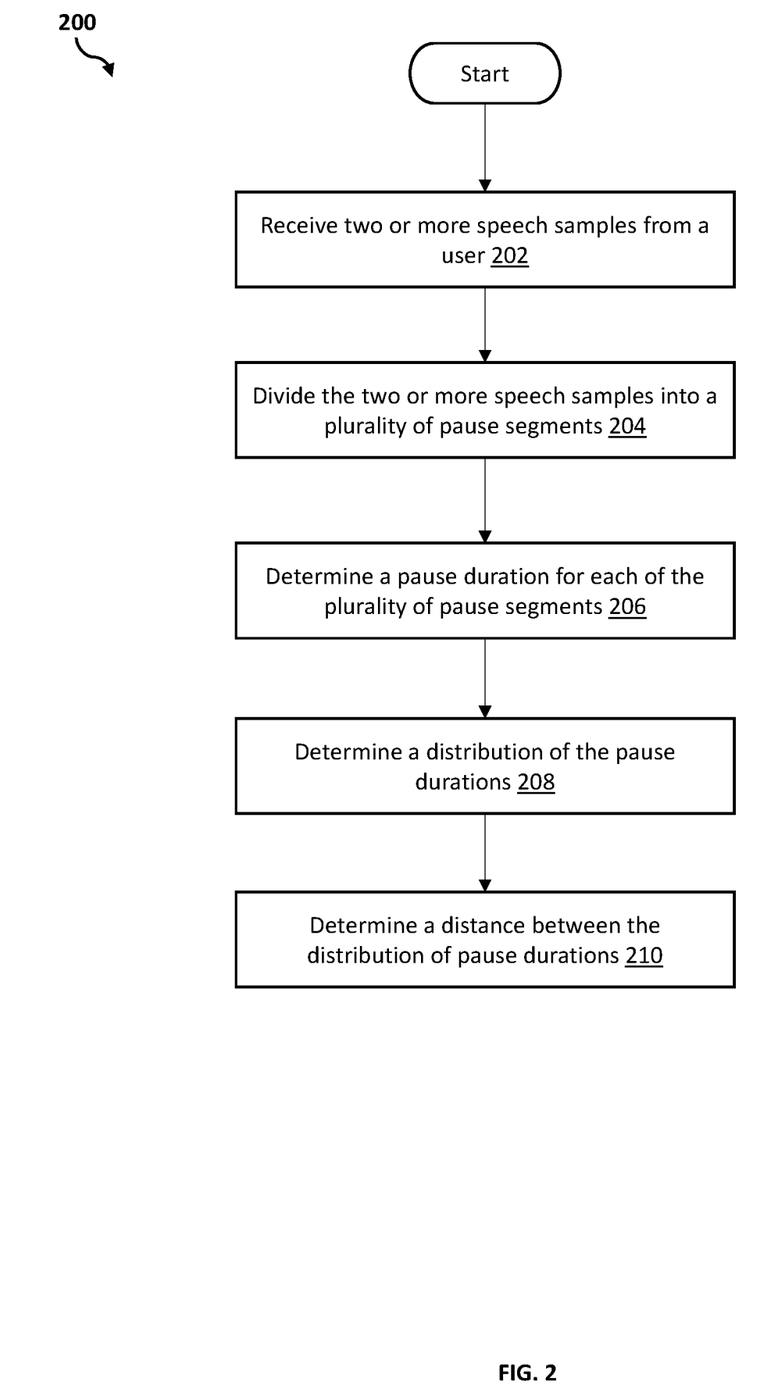
FIG. 2 is an operational flowchart illustrating a process for speech feature distribution according to at least one embodiment.

Referring now to FIG. 2, an operational flowchart illustrating the exemplary speech feature distribution process 200 used by the speech feature program 110a and 110b (hereinafter speech feature program 110) according to at least one embodiment is depicted.

At 202, the speech feature program 110 receives two or more speech samples from a user. The speech feature program 110 may receive a speech sample for each task the user performs. Each of the two or more tasks the user may perform may be a cognitive and/or neuropsychological task accessed from a knowledge corpus (e.g., database 114). Each of the two or more tasks in which the speech feature program 110 receives the speech samples may be of a different difficulty level.

The knowledge corpus (e.g., database 114) may include a plurality of speech features obtained from a plurality of individuals for a plurality of cognitive and/or neuropsychological tasks. The plurality of speech features may include, but are not limited to including, pause duration, pause frequency, and/or latency to response recorded for the individuals for the cognitive and/or neuropsychological tasks. The individuals from whom the speech features may be obtained may include, but are not limited to including, individuals with a diagnosed cognitive impairment and/or individuals with no diagnosed cognitive impairment. The knowledge corpus (e.g., database 114) may also include additional data with respect to the individuals with the diagnosed cognitive impairment, such as, but not limited to, stages of dementia using the Global Deterioration Scale (GDS) and/or Reisberg Scale, symptoms of cognitive impairments, treatments undergone, one or more scores for clinical cognitive tests, Mini-Mental State Examination (MMSE) data, Montreal Cognitive Assessment (MoCA) data, amongst other additional data. The speech feature program 110 may only include speech features in the knowledge corpus (e.g., database 114) from individuals who directly consented to and/or from whom consent was received by another individual with legal authority (e.g., individual's representative) to consent on behalf of the individual. The plurality of speech features obtained from the individual and/or any other data received from the individual by the speech feature program 110 shall not be construed as to violate and/or encourage the violation of any local, state, federal, or international law with respect to data privacy protection. The speech feature program 110 may only store data, in the knowledge corpus (e.g., database 114), for which consent was received and/or may not store any additional data beyond that which may be necessary. The speech feature program 110 may intermittently confirm with the individual and/or the individual's representative as to whether the speech feature program 110 may maintain at least the speech features obtained and/or other relevant data within the knowledge corpus (e.g., database 114).

In an embodiment, the speech feature program 110 may utilize the plurality of speech features obtained from the plurality of individuals in generating representative speech features. The representative speech features may not correspond to an individual but rather may be based on the plurality of speech features previously obtained. The speech feature program 110 may generate the representative speech features such that the speech feature program 110 may reduce the number of individuals in which speech features and/or data may be obtained.

The two or more speech samples received by the speech feature program 110 from the user may each correspond to a task selected from the knowledge corpus (e.g., database 114). The speech feature program 110 may select the two or more tasks from the knowledge corpus (e.g., database 114) based on speech features obtained from two or more similar individuals to the user. The speech feature program 110 may select at least one similar individual with a diagnosed cognitive impairment and one similar individual with no diagnosed cognitive impairment. The speech feature program 110 may determine the two or more similar individuals based on data received and/or accessed for the user and data stored with respect to the plurality of individuals of which speech features may be stored in the knowledge corpus (e.g., database 114). In an embodiment, the speech feature program 110 may receive input from a medical professional such as, but not limited to, a psychometrist, a speech pathologist, and/or neuropsychologist in determining the two or more similar individuals and/or the two or more tasks from the knowledge corpus (e.g., database 114).

The speech feature program 110 may enable the medical professional to select the two or more similar individuals and/or the two or more tasks from the knowledge corpus in a speech user interface 118. In an embodiment, the speech feature program 110 may receive data input from the medical professional responsible in treating the user. The data input received may be utilized by the speech feature program 110 in identifying the two or more similar individuals and/or the two or more tasks. The speech user interface 118 may allow the medical professional to adjust the two or more tasks to be performed by the user prior to the speech feature program 110 receiving the two or more speech samples from the user. The speech user interface 118 may be displayed by the speech feature program 110 in at least an internet browser, dedicated software application, or as an integration with a third party software application.

Each of the two or more speech samples received from the user by the speech feature program 110 for the two or more tasks may be of a different difficulty level. As will be explained in more detail below with respect to step 210, the speech feature program 110 may utilize a distance between each distribution of a pause duration of the two or more speech samples such that the difference in the difficulty level for the two or more tasks may not require quantification. The speech feature program 110 may not require quantification of the difference in difficulty because the speech feature program 110 may utilize the sensitivity of the user to differences in the two or more cognitive tasks, as measured by the distance between the distributions of pause durations, as an indicator of the probability in which the user is suffering from a cognitive impairment. For example, the speech feature program 110 may receive two speech samples from User 1. Speech sample 1 may be for Task 1 of the user counting backwards in increments of 5 from 100. Speech sample 2 may be for Task 2 of the user counting backwards in increments of 7 from 110. In this example, Task 1 for speech sample 1 may be less difficult than Task 2 for speech sample 2 but the degree to which Task 2 may be more difficult than Task 1 may not be quantifiable.

In other embodiments, the speech feature program 110 may receive two or more speech samples from the user with different difficulty levels, however, the difference in difficulty levels may be unquantifiable. As will be explained in more detail below, in these embodiments the pause durations derived from the two or more speech samples with unquantifiable difficulty levels may still be utilized in identifying consistent differences in pause durations. For example, the speech feature program 110 may receive two speech samples from the user. Speech sample 1 may be for the task of the user saying as many animal names as possible. Speech sample 2 may be for the user saying as many words starting with the letter "a" as possible. In this example, the tasks are similar but the difference in difficulty between the tasks is unknown but may be utilized by the speech feature program 110 in identifying a consistent difference which may depend on a severity of a cognitive impairment. As will be explained in more detail below with respect to step 210, the consistent difference may be the difference between each distribution of the pause duration for individuals with a cognitive impairment versus the distance between each distribution of the pause duration with no cognitive impairment. The consistent difference may be at least one of the plurality of speech features stored in the knowledge corpus (e.g., database 114). In another example, the speech feature program 110 may receive two speech samples from the user. Speech sample 1 may be for the task of the user saying as many animal names as possible. Speech sample 2 may be for the user to describe a picture as detailed as possible. In this example, the tasks are dissimilar but the speech recognition program 110 may utilize pause duration in identifying a consistent difference which may depend on a severity of a cognitive impairment.

The examples given above may be illustrative of the scope of the speech feature program 110 but may not be limiting. These examples may illustrate that the speech feature program 110 may be applicable to a wide variety of cognitive and/or neuropsychological tasks for which the task difficulty may be unquantifiable, and the two or more tasks may be dissimilar.

In an embodiment, the speech feature program 110 may receive a first speech sample and select a second task from the knowledge corpus (e.g., database 114) based on an analysis of the first speech sample for a first task. For example, the speech feature program 110 may receive user data input from a medical professional responsible for treating the user. The speech feature program 110 may retrieve two lists of similar individuals who have performed a task based on the data input of the medical professional. The first list may be comprised of individuals with a diagnosed cognitive impairment and the second list may be comprised of individuals with no diagnosed cognitive impairment. The speech feature program 110 may present both lists to the medical professional in the speech user interface 118. The medical professional may select an individual from the first list and the second list who have both performed the same task. In this example, the medical professional may have additional data with respect to the user not provided as input for the speech feature program 110 such that the medical professional may determine the individual from the first list and the second list based on the two lists of similar individuals provided by the speech feature program 110. The speech feature program 110 may retrieve the task in which both the first individual and the second individual performed. The task criteria may be displayed to the medical professional within the speech feature user interface 118. The medical professional may choose to modify the task within the speech user interface 118 prior to performance of the task by the user. The speech feature program 110 may then receive a speech sample of the user for the task. The speech feature program 110 may analyze the speech sample utilizing one or more speech-to-text engines which will be explained in more detail below with respect to step 204. In this example, the speech feature program 110 may select the second task from the knowledge corpus (e.g., database 114) based on at least speech features, such as, but not limited to, pause durations, determined from the analysis utilizing the one or more speech-to-text engines. The speech feature program 110 may select a second task easier than the first task if the pause durations of the speech sample for the first task were similar to those of the similar individual with a cognitive impairment and may select a second task more difficult than the first task if the pause durations of the speech sample for the first task were similar to those of the similar individual with no cognitive impairment.

At 204, the speech feature program 110 divides the two or more speech samples from the user into a plurality of pause segments. The speech feature program 110 may divide the two or more speech samples from the user into utterance segments and pause segments utilizing one or more speech-to-text engines.

The one or more speech-to-text engines utilized by the speech feature program 110 may include, but are not limited to including, IBM Watson® Text to Speech (IBM Watson® and all Watson-based trademarks are trademarks or registered trademarks of International Business Machines Corporation in the United States, and/or other countries), IBM Watson® Speech Recognition, IBM Watson® Natural Language Understanding, IBM Watson® Natural Language Processing, amongst other speech-to-text engines. The speech feature program 110 may utilize a Voice Activity Detection (VAD) feature of the one or more speech-to-text engines in dividing the two or more speech samples into the utterance segments and the pause segments. The speech feature program 110 may also utilize additional audio features in silence detection, such as, but not limited to Root Mean Square (RMS) and/or Spectral Power (SP), amongst other audio features in silence detection.

Utilizing the VAD feature of the one or more speech-to-text engines the speech feature program 110 may determine the pause segments using a sound intensity level threshold, wherein the sound intensity level at a time point, t [s], is smaller than the sound intensity level threshold, A [dB]. The speech to feature program 110 may utilize at least, seconds [s], centiseconds [cs], milliseconds [ms], amongst other units to measure the pause duration. The speech feature program 110 may utilize decibels [dB] amongst other units of measure for sound intensity and/or amplitude in monitoring the sound level intensity threshold.

The sound intensity level threshold utilized by the speech feature program 110 may utilize a default threshold, such as 25 decibels [dB], which may be determined by the speech feature program 110 utilizing one or more audio classification and/or segmentation algorithms. The sound intensity level threshold may also be adjusted by the medical professional in the speech user interface 118.

At 206, the speech feature program 110 determines a pause duration for each of the pause segments of the two or more speech samples. The speech feature program 110 may determine the pause duration for each of the pause segments identified in step 204 based on a length of time the sound intensity level remained below the sound intensity level threshold. The speech feature program 110 may utilize at least, seconds [s], centiseconds [cs], milliseconds [ms], amongst other units to measure the pause duration.

For example, the speech feature program 110 may receive two speech samples from the user. Speech Sample 1 may be for Task 1 and Speech Sample 2 may be for Task 2. The speech feature program 110 may divide Speech Sample 1 into a plurality of utterance segments and a plurality of pause segments utilizing the VAD feature of the one or more speech-to-text engines described above, wherein the plurality of pause segments may be segments in which the Speech Sample 1 has a sound intensity level threshold below 25 decibels [dB]. Accordingly, the speech feature program 110 may determine the length of each the plurality of pause segments. In this example, if Task 1 is for the user to count backwards in increments of 2 from 10, the plurality of pause segments may be the pause durations between the user responding 8, 6, 4, 2, and 0. The speech feature program 110 may utilize milliseconds and/or other units of measure in measuring the plurality of pause segments.

At 208, the speech feature program 110 determines a distribution of the pause duration for each of the two or more speech samples. The speech feature program 110 may determine the distribution of the pause duration for each of the two or more speech samples utilizing one or more hyperparameter optimization methods.

The speech feature program 110 may utilize the one or more hyperparameter optimization methods in determining the distribution of pause duration to be utilized by one or more machine learning models as will be explained in more detail below. The speech feature program 110 may utilize hyperparameter optimization methods, such as, but not limited to grid search, random search, Bayesian optimization, gradient-based optimization, evolutionary optimization, population-based training (PBT), early stopping-based, amongst other hyperparameter optimization methods in determining the distribution of the pause duration based on the plurality of pause durations stored in the knowledge corpus (e.g., database 114).

At 210, the speech feature program 110 determines a distance between each distribution of the pause duration of the two or more speech samples. The speech feature program 110 may determine the distance between each distribution of the pause duration of the two or more speech samples as a feature utilizing one or more distribution techniques. The distance between each distribution of the pause duration may be utilized by the speech feature program 110 as a stand alone indicator of cognitive impairment and/or as input for one or more machine learning models, as will be explained in more detail below.

The speech feature program 110 may utilize one or more distribution techniques in determining the distance between each distribution of the pause duration of the two or more speech samples. The one or more distribution techniques, may include, but are not limited to including Jensen-Shannon divergence, Kullback-Leibler divergence, Kolmogorv-Smirnov statistic, Wasserstein distance, difference in mean, difference in standard deviation, amongst other distribution techniques. The speech feature program 110 may determine which of the one or more distribution techniques to be utilized based on at least the two or more tasks performed by the user and/or the speech feature to be utilized. The speech feature program 110 may utilize the one or more distribution techniques with the highest area under the curve (AUC) and/or lowest p-value. For example, in the Jensen-Shannon divergence may discriminate between the mean and confidence interval for AUC and a healthy control (HC) more efficiently for the distance of pause durations between two tasks than difference of mean, difference of standard deviation, and/or Wasserstein distance as measured according to p-value and/or AUC. The one or more distribution techniques may distinguish the user between individuals with and without the cognitive impairment. The confidence interval for the mean may be utilized by the speech feature program 110 as opposed to a single number for the mean, the confidence interval may enable the speech feature program 110 to utilize a lower estimate and/or an upper estimate for the parameters of the knowledge base (e.g., database 114).

The distance between each distance between the distribution of pause durations may be utilized in detecting sensitivity of the user to differences in cognitive tasks which may more accurately indicate the probability in which the user may be suffering from a cognitive impairment than pause duration alone which may be susceptible to inter-individual variability.

At 212, the speech feature program 110 determines the probability in which the user is suffering from a cognitive impairment. The speech feature program 110 may determine the probability in which the user is suffering from a cognitive impairment based on the distance between each distribution of the pause duration of the two or more speech samples. The pause duration may be utilized by the speech feature program 110 as a stand-alone indicator of the cognitive impairment and/or as input for one or more machine learning models.

The speech feature program 110 may utilize the distance between each distribution of the pause duration for the two or more speech samples as a stand-alone indicator in which it may be compared with the distances between pause durations stored within the knowledge corpus (e.g., database 114). The speech feature program 110 may determine the probability in which the user is suffering from a cognitive impairment based on the similarity of the distribution of pause durations of the user to distributions of pause durations of similar individuals stored within the knowledge corpus (e.g., database 114).

The speech feature program 110 may determine the probability in which the user is suffering from a cognitive impairment based on at least the distance between each distribution of the pause duration of the two or more speech samples. The speech feature program 110 may also utilize additional speech features, such as, but not limited to, pause frequency and/or latency to response, and/or user data input by the medical professional, in determining the probability in which the user is suffering from a cognitive impairment.

The speech feature program 110 may utilize one or more of, the distance between each distribution of the pause duration, additional speech features, and/or user data as input for one or more machine learning models in determining the probability in which the user is suffering from the cognitive impairment. The speech feature program 110 may utilize one or more algorithms in building the one or more machine learning models, the one or more algorithms may include, but are not limited to including, classification and/or regression models. The one or more machine learning models may utilize learning algorithms such as, but not limited to, logistic/linear regression algorithms, random forest, support vector machines, k-nearest neighbors, and/or gaussian process, amongst other algorithms which may be utilized in building the one or more machine learning models utilized in determining the probability in which the user may be suffering from the cognitive impairment. The one or more machine learning models being trained based on the plurality of speech features and/or other relevant data stored the knowledge corpus (e.g., database 114) and/or publicly available datasets for individuals with mild cognitive impairment and/or Alzheimer's disease, using one or more model training processes, such as, but not limited to a holdout and/or cross validation method.

In an embodiment, the classification models may be trained to classify the user as either an individual with a cognitive impairment or an individual without a cognitive impairment and produce an output indicator of the probability. The output indicator may be a probability score indicating the probability in which the user is suffering from the cognitive impairment. The regression models may be trained to estimate the user's cognitive score, such as the Mini-Mental State Examination score and/or Montreal Cognitive Assessment score. The regression models may output the estimated cognitive score as an indicator of the severity in which the user is suffering the cognitive impairment. The speech feature program 110 may leverage the probability score, cognitive score, and/or additional data in determining the probability in which the user is suffering from the cognitive impairment.

The speech feature program 110 may also determine which cognitive impairment the user may be suffering from, a stage of the cognitive impairment from which the user may be suffering from, and/or one or more recommendations for the user based on at least the cognitive impairment and/or the stage of the cognitive impairment. The speech feature program 110 may utilize the one or more machine learning models and the input described above in determining which cognitive impairment, the stage of the cognitive impairment, and/or one or more recommendations for the user.

The speech feature program 110 may provide one or more recommendations to the user and/or a medical professional based on at least the probability in which the user is suffering from the cognitive impairment, which cognitive impairment the user is suffering from, and/or the stage of the cognitive impairment. The speech feature program 110 may display the one or more recommendations to the user and/or the medical professional in a speech user interface 118. The one or more recommendations may be based on the efficacy of treatments for similar individuals stored in the knowledge corpus (e.g., database 114).

It may be appreciated that FIG. 2 provides only an illustration of one embodiment and do not imply any limitations with regard to how different embodiments may be implemented. Many modifications to the depicted embodiment(s) may be made based on design and implementation requirements.

Figure 3:
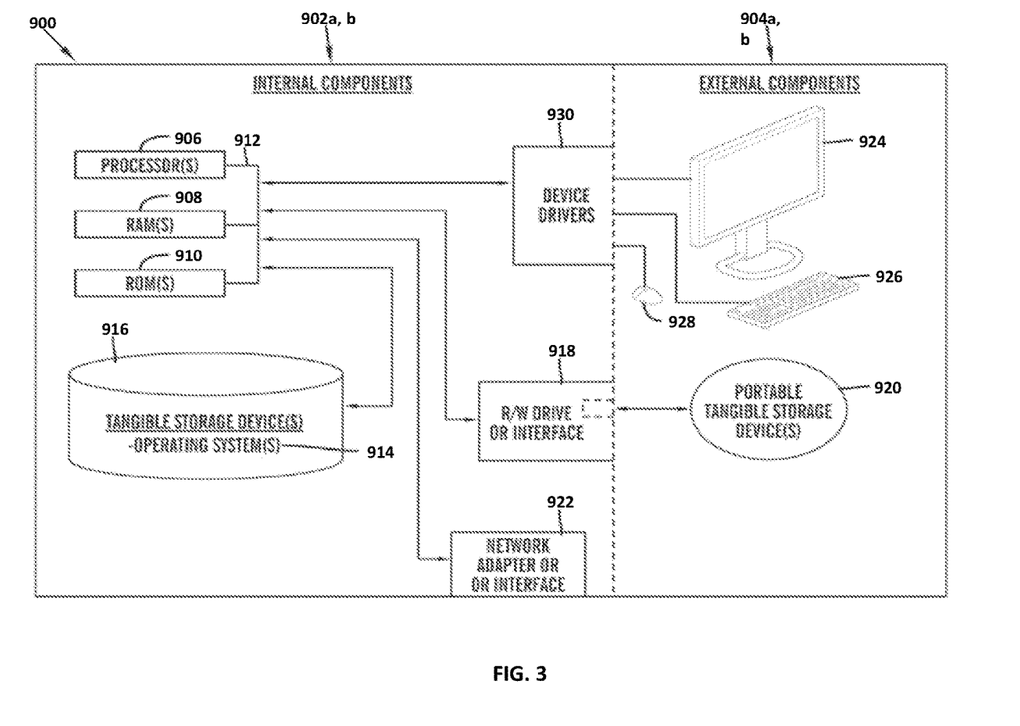
FIG. 3 is a block diagram of internal and external components of computers and servers depicted in FIG. 1 according to at least one embodiment.

FIG. 3 is a block diagram 900 of internal and external components of computers depicted in FIG. 1 in accordance with an illustrative embodiment of the present invention. It should be appreciated that FIG. 3 provides only an illustration of one implementation and does not imply any limitations with regard to the environments in which different embodiments may be implemented. Many modifications to the depicted environments may be made based on design and implementation requirements.

Data processing system 902, 904 is representative of any electronic device capable of executing machine-readable program instructions. Data processing system 902, 904 may be representative of a smart phone, a computer system, PDA, or other electronic devices. Examples of computing systems, environments, and/or configurations that may be represented by data processing system 902, 904 include, but are not limited to, personal computer systems, server computer systems, thin clients, thick clients, hand-held or laptop devices, multiprocessor systems, microprocessor-based systems, network PCs, minicomputer systems, and distributed cloud computing environments that include any of the above systems or devices.

User client computer 102 and network server 112 may include respective sets of internal components 902*a, b* and external components 904*a, b* illustrated in FIG. 3. Each of the sets of internal components 902*a, b* includes one or more processors 906, one or more computer-readable RAMs 908 and one or more computer-readable ROMs 910 on one or more buses 912, and one or more operating systems 914 and one or more computer-readable tangible storage devices

916. The one or more operating systems 914, the software program 108, and the speech feature program 110*a* in client computer 102, and the speech feature program 110*b* in network server 112, may be stored on one or more computer-readable tangible storage devices 916 for execution by one or more processors 906 via one or more RAMs 908 (which typically include cache memory). In the embodiment illustrated in FIG. 3, each of the computer-readable tangible storage devices 916 is a magnetic disk storage device of an internal hard drive. Alternatively, each of the computer-readable tangible storage devices 916 is a semiconductor storage device such as ROM 910, EPROM, flash memory or any other computer-readable tangible storage device that can store a computer program and digital information.

Each set of internal components 902*a, b* also includes a R/W drive or interface 918 to read from and write to one or more portable computer-readable tangible storage devices 920 such as a CD-ROM, DVD, memory stick, magnetic tape, magnetic disk, optical disk or semiconductor storage device. A software program, such as the software program 108 and the speech feature program 110*a* and 110*b* can be stored on one or more of the respective portable computer-readable tangible storage devices 920, read via the respective R/W drive or interface 918 and loaded into the respective hard drive 916.

Each set of internal components 902*a, b* may also include network adapters (or switch port cards) or interfaces 922 such as a TCP/IP adapter cards, wireless wi-fi interface cards, or 3G or 4G wireless interface cards or other wired or wireless communication links. The software program 108 and the speech feature program 110*a* in client computer 102 and the speech feature program 110*b* in network server computer 112 can be downloaded from an external computer (e.g., server) via a network (for example, the Internet, a local area network or other, wide area network) and respective network adapters or interfaces 922. From the network adapters (or switch port adaptors) or interfaces 922, the software program 108 and the speech feature program 110*a* in client computer 102 and the speech feature program 110*b* in network server computer 112 are loaded into the respective hard drive 916. The network may comprise copper wires, optical fibers, wireless transmission, routers, firewalls, switches, gateway computers and/or edge servers.

Each of the sets of external components 904*a, b* can include a computer display monitor 924, a keyboard 926, and a computer mouse 928. External components 904*a, b* can also include touch screens, virtual keyboards, touch pads, pointing devices, and other human interface devices. Each of the sets of internal components 902*a, b* also includes device drivers 930 to interface to computer display monitor 924, keyboard 926 and computer mouse 928. The device drivers 930, R/W drive or interface 918 and network adapter or interface 922 comprise hardware and software (stored in storage device 916 and/or ROM 910).

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 4:
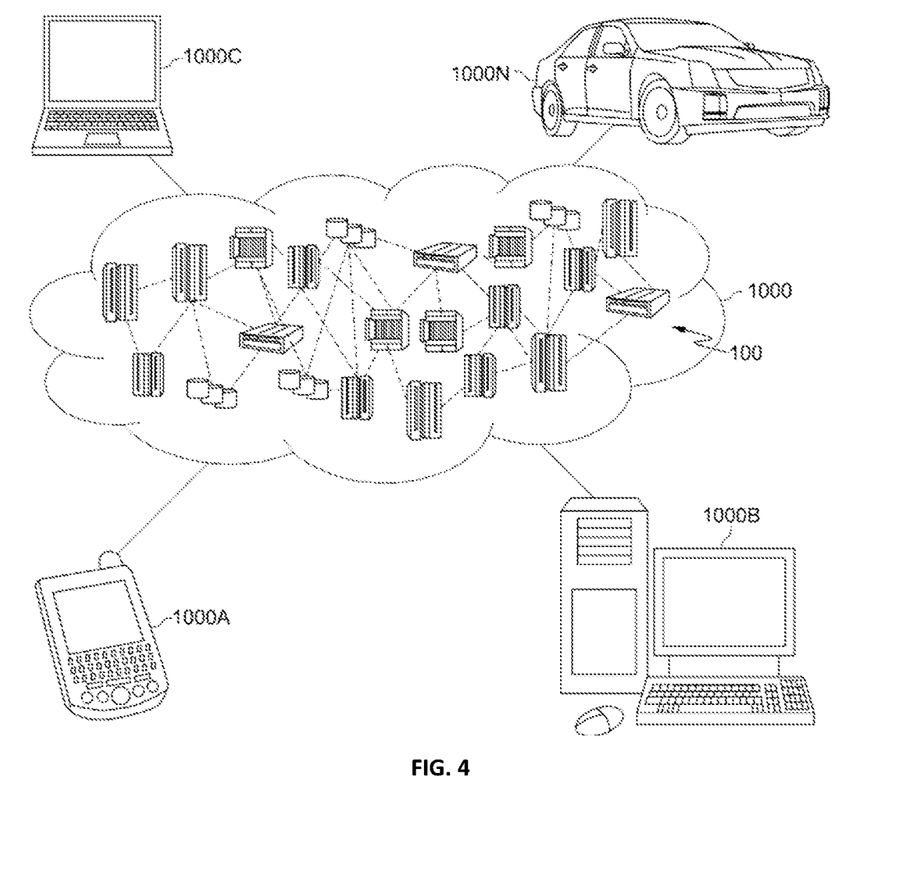
FIG. 4 is a block diagram of an illustrative cloud computing environment including the computer system depicted in FIG. 1, in accordance with an embodiment of the present disclosure.

Referring now to FIG. 4, illustrative cloud computing environment 1000 is depicted. As shown, cloud computing environment 1000 comprises one or more cloud computing nodes 100 with which local computing devices used by cloud consumers, such as, for example, personal digital assistant (PDA) or cellular telephone 1000A, desktop computer 1000B, laptop computer 1000C, and/or automobile computer system 1000N may communicate. Nodes 100 may communicate with one another. They may be grouped (not shown) physically or virtually, in one or more networks, such as Private, Community, Public, or Hybrid clouds as described hereinabove, or a combination thereof. This allows cloud computing environment 1000 to offer infrastructure, platforms and/or software as services for which a cloud consumer does not need to maintain resources on a local computing device. It is understood that the types of computing devices 1000A-N shown in FIG. 4 are intended to be illustrative only and that computing nodes 100 and cloud computing environment 1000 can communicate with any type of computerized device over any type of network and/or network addressable connection (e.g., using a web browser).

Figure 5:
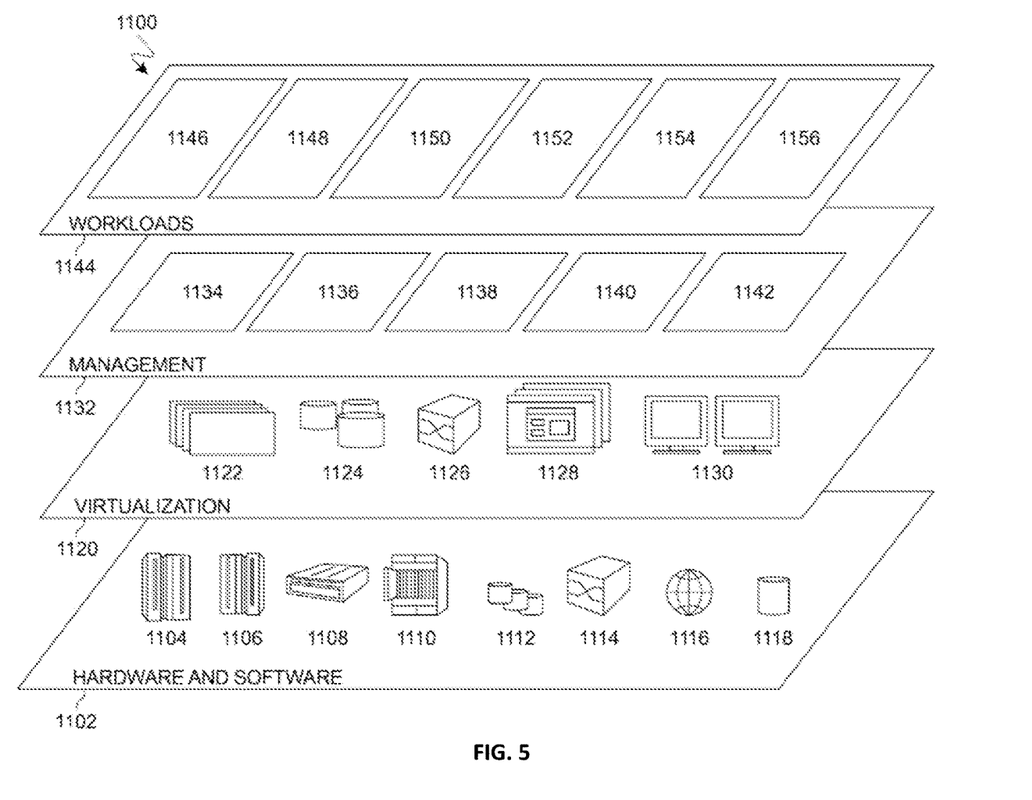
FIG. 5 is a block diagram of functional layers of the illustrative cloud computing environment of FIG. 4, in accordance with an embodiment of the present disclosure.

Referring now to FIG. 5, a set of functional abstraction layers 1100 provided by cloud computing environment 1000 is shown. It should be understood in advance that the components, layers, and functions shown in FIG. 5 are intended to be illustrative only and embodiments of the invention are not limited thereto. As depicted, the following layers and corresponding functions are provided:

Hardware and software layer 1102 includes hardware and software components. Examples of hardware components include: mainframes 1104; RISC (Reduced Instruction Set Computer) architecture based servers 1106; servers 1108; blade servers 1110; storage devices 1112; and networks and networking components 1114. In some embodiments, software components include network application server software 1116 and database software 1118.

Virtualization layer 1120 provides an abstraction layer from which the following examples of virtual entities may be provided: virtual servers 1122; virtual storage 1124; virtual networks 1126, including virtual private networks; virtual applications and operating systems 1128; and virtual clients 1130.

In one example, management layer 1132 may provide the functions described below. Resource provisioning 1134 provides dynamic procurement of computing resources and other resources that are utilized to perform tasks within the cloud computing environment. Metering and Pricing 1136 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 1138 provides access to the cloud computing environment for consumers and system administrators. Service level management 1140 provides cloud computing resource allocation and management such that required service levels are met. Service Level Agreement (SLA) planning and fulfillment 1142 provide pre-arrangement for, and procurement of, cloud computing resources for which a future requirement is anticipated in accordance with an SLA.

Workloads layer 1144 provides examples of functionality for which the cloud computing environment may be utilized. Examples of workloads and functions which may be provided from this layer include: mapping and navigation 1146; software development and lifecycle management 1148; virtual classroom education delivery 1150; data analytics processing 1152; transaction processing 1154; and speech feature program 1156. A speech feature program 110a, 110b provides a way to generate quantitative indicators of cognitive impairment based on distances between distributions of speech features extracted from two or more tasks.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope of the described embodiments. The terminology used herein was chosen to best explain the principles of the embodiments, the practical application or technical improvement over technologies found in the marketplace, or to enable others of ordinary skill in the art to understand the embodiments disclosed herein.

The present disclosure shall not be construed as to violate or encourage the violation of any local, state, federal, or international law with respect to privacy protection.

What is claimed is:

1. A method for speech feature distribution, the method comprising:

receiving two or more speech samples from a user, wherein a first speech sample corresponds to a first task, wherein a second speech sample corresponds to a second task, and wherein the first task and the second task are each one of at least two or more tasks selected by a medical professional within a speech user interface, wherein each of the at least two or more tasks are retrieved from a knowledge corpus and are of different cognitive difficulty levels;

dividing at least the first speech sample and the second speech sample into a plurality of pause segments using a Voice Activity Detection (VAD) feature of one or more speech-to-text engines, wherein the plurality of pause segments are below a sound intensity level threshold set or adjusted by the medical professional in the speech user interface;

determining a first pause duration distribution from the plurality of pause segments of the first speech sample;

determining a second pause duration distribution from the plurality of pause segments of the second speech sample;

determining a distance between the first pause duration distribution and the second pause duration distribution; and comparing the distance with a corresponding distance between pause duration distributions from a second user for a same at least two or more tasks, wherein the second user has a cognitive impairment.

2. The method of claim 1, further comprising:

determining a probability in which the user is suffering from the cognitive impairment of the second user based on the comparing of the distance between each of the distributions of the pause durations of the two or more speech samples received for the user and the second user, wherein the distributions of the pause durations for the second user are retrieved from the knowledge corpus.

3. The method of claim 2, further comprising:

displaying one or more recommendations to the medical professional within the speech user interface based on the probability in which the user is suffering from the cognitive impairment, wherein the one or more recommendations are based on an efficacy of treatments for the second user stored in the knowledge corpus.

4. The method of claim 1, wherein selecting the first task and the second task from the knowledge corpus further comprises:

retrieving at least two lists of similar individuals who have performed a same task, based on data input received from the medical professional with respect to the user, the data input being entered by the user in the speech user interface;

displaying the at least two lists of similar individuals to the medical professional in the speech user interface;

displaying the first task and the second task to the medical professional in the speech user interface based on the similar individuals selected by the medical professional from the at least two lists; and adjusting the first task and the second task based on a modification of the medical professional.

5. The method of claim 1, further comprising:

determining a probability in which the user is suffering from at least one cognitive impairment of a plurality of cognitive impairments using one or more machine learning models, wherein the one or more machine learning models are trained according to a holdout or cross validation method and are based on a plurality of speech features and plurality of data stored in the knowledge corpus, wherein an input received by the one or more machine learning models is selected from the group consisting of the distance between the distribution of the pause durations for the user, a plurality of additional speech features determined from the two or more speech samples of the user, and a plurality of user data inputted by the medical professional.

6. The method of claim 5, further comprising:

determining, using the one or more machine learning models, which of the plurality of cognitive impairments the user is suffering from;

determining, using the one or more machine learning models, a stage of the at least one cognitive impairment; and providing, in the speech user interface, one or more recommendations to the user for the at least one cognitive impairment, wherein the one or more recommendations are determined using the one or more machine learning models utilizing as input at least, one or more of, which of the plurality of cognitive impairments the user is suffering from, the stage of the at least one cognitive impairment, and data stored in the knowledge corpus.

7. The method of claim 1, wherein the distance between each of the distributions for each of the pause durations is determined utilizing one or more distribution techniques, wherein the one or more distribution techniques are selected based on the tasks selected by the medical professional, a highest area under a curve (AUC), and a lowest p value.

8. A computer system for speech feature distribution, comprising:

one or more processors, one or more computer-readable memories, one or more computer-readable tangible storage medium, and program instructions stored on at least one of the one or more tangible storage medium for execution by at least one of the one or more processors via at least one of the one or more memories, wherein the computer system is capable of performing a method comprising:

receiving two or more speech samples from a user, wherein a first speech sample corresponds to a first task, wherein a second speech sample corresponds to a second task, and wherein the first task and the second task are each one of at least two or more tasks selected by a medical professional within a speech user interface, wherein each of the at least two or more tasks are retrieved from a knowledge corpus and are of different cognitive difficulty levels;

dividing at least the first speech sample and the second speech sample into a plurality of pause segments using a Voice Activity Detection (VAD) feature of one or more speech-to-text engines, wherein the plurality of pause segments are below a sound intensity level threshold set or adjusted by the medical professional in the speech user interface;

determining a first pause duration distribution from the plurality of pause segments of the first speech sample;

determining a second pause duration distribution from the plurality of pause segments of the second speech sample;

determining a distance between the first pause duration distribution and the second pause duration distribution; and comparing the distance with a corresponding distance between pause duration distributions from a second user for a same at least two or more tasks, wherein the second user has a cognitive impairment.

9. The computer system of claim 8, further comprising:

determining a probability in which the user is suffering from the cognitive impairment of the second user based on the comparing of the distance between each of the distributions of the pause durations of the two or more speech samples received for the user and the second user, wherein the distributions of the pause durations for the second user are retrieved from the knowledge corpus.

10. The computer system of claim 9, further comprising:

displaying one or more recommendations to the medical professional within the speech user interface based on the probability in which the user is suffering from the cognitive impairment, wherein the one or more recommendations are based on an efficacy of treatments for the second user stored in the knowledge corpus.

11. The computer system of claim 8, wherein selecting the first task and the second task from the knowledge corpus further comprises:

retrieving at least two lists of similar individuals who have performed a same task, based on data input received from the medical professional with respect to the user, the data input being entered by the user in the speech user interface;

displaying the at least two lists of similar individuals to the medical professional in the speech user interface;

displaying the first task and the second task to the medical professional in the speech user interface based on the similar individuals selected by the medical professional from the at least two lists; and adjusting the first task and the second task based on a modification of the medical professional.

12. The computer system of claim 8, further comprising:

determining a probability in which the user is suffering from at least one of a plurality of cognitive impairments using one or more machine learning models, wherein the one or more machine learning models are trained according to a holdout or cross validation method and are based on a plurality of speech features and plurality of data stored in the knowledge corpus, wherein an input received by the one or more machine learning models is selected from the group consisting of the distance between the distribution of the pause durations for the user, a plurality of additional speech features determined from the two or more speech samples of the user, and a plurality of user data inputted by the medical professional.

13. The computer system of claim 12, further comprising:

determining, using the one or more machine learning models, which of the plurality of cognitive impairments the user is suffering from;

determining, using the one or more machine learning models, a stage of the at least one cognitive impairment; and providing, in the speech user interface, one or more recommendations to the user for the at least one cognitive impairment, wherein the one or more recommendations are determined using the one or more machine learning models utilizing as input at least, one or more of, which of the plurality of cognitive impairments the user is suffering from, the stage of the at least one cognitive impairment, and data stored in the knowledge corpus.

14. The computer system of claim 8, wherein the distance between each of the distributions for each of the pause durations is determined utilizing one or more distribution techniques, wherein the one or more distribution techniques are selected based on the tasks selected by the medical professional, a highest area under a curve (AUC), and a lowest p value.

15. A computer program product for speech feature distribution, comprising:

one or more non-transitory computer-readable storage media and program instructions stored on at least one of the one or more tangible storage media, the program instructions executable by a processor to cause the processor to perform a method comprising:

receiving two or more speech samples from a user, wherein a first speech sample corresponds to a first task, wherein a second speech sample corresponds to a second task, and wherein the first task and the second task are each one of at least two or more tasks selected by a medical professional within a speech user interface, wherein each of the at least two or more tasks are retrieved from a knowledge corpus and are of different cognitive difficulty levels;

dividing at least the first speech sample and the second speech sample into a plurality of pause segments using a Voice Activity Detection (VAD) feature of one or more speech-to-text engines, wherein the plurality of pause segments are below a sound intensity level threshold set or adjusted by the medical professional in the speech user interface;

determining a first pause duration distribution from the plurality of pause segments of the first speech sample;

determining a second pause duration distribution from the plurality of pause segments of the second speech sample;

determining a distance between the first pause duration distribution and the second pause duration distribution; and comparing the distance with a corresponding distance between pause duration distributions from a second user for a same at least two or more tasks, wherein the second user has a cognitive impairment.

16. The computer program product of claim 15, further comprising:

determining a probability in which the user is suffering from the cognitive impairment of the second user based on the comparing of the distance between each of the distributions of the pause durations of the two or more speech samples received for the user and the second user, wherein the distributions of the pause durations for the second user are retrieved from the knowledge corpus.

17. The computer program product of claim 16, further comprising:

displaying one or more recommendations to the medical professional within the speech user interface based on the probability in which the user is suffering from the cognitive impairment, wherein the one or more recommendations are based on an efficacy of treatments for the second user stored in the knowledge corpus.

18. The computer program product of claim 15, wherein selecting the first task and the second task from the knowledge corpus further comprises:

retrieving at least two lists of similar individuals who have performed a same task, based on data input received from the medical professional with respect to the user, the data input being entered by the user in the speech user interface;

displaying the at least two lists of similar individuals to the medical professional in the speech user interface;

displaying the first task and the second task to the medical professional in the speech user interface based on the similar individuals selected by the medical professional from the at least two lists; and adjusting the first task and the second task based on a modification of the medical professional.

19. The computer program product of claim 15, further comprising:

determining a probability in which the user is suffering from at least one of a plurality of cognitive impairments using one or more machine learning models, wherein the one or more machine learning models are trained according to a holdout or cross validation method and are based on a plurality of speech features and plurality of data stored in the knowledge corpus, wherein an input received by the one or more machine learning models is selected from the group consisting of the distance between the distribution of the pause durations for the user, a plurality of additional speech features determined from the two or more speech samples of the user, and a plurality of user data inputted by the medical professional.

20. The computer program product of claim 15, wherein the distance between each of the distributions for each of the pause durations is determined utilizing one or more distribution techniques, wherein the one or more distribution techniques are selected based on the tasks selected by the medical professional, a highest area under a curve (AUC), and a lowest p value.

* * * * *